US00PP34019P3

(12) United States Plant Patent
Schoone

(10) Patent No.: US PP34,019 P3
(45) Date of Patent: Mar. 15, 2022

(54) **X *DORITAENOPSIS* PLANT NAMED 'LADY FANTASY'**

(50) Latin Name: **x *Doritaenopsis (Doritis* x *Phalaenopsis)***
Varietal Denomination: Lady Fantasy

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/340,015

(22) Filed: Jun. 5, 2021

(65) Prior Publication Data

US 2021/0386003 P1 Dec. 9, 2021

Related U.S. Application Data

(60) Provisional application No. 62/705,005, filed on Jun. 6, 2020.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Doritaenopsis* plant named 'Lady Fantasy', characterized by its upright plant habit; moderately vigorous to vigorous growth habit; strong leaves; strong flowering stems; freely flowering habit with typically two inflorescences per plant, each inflorescence with numerous flowers; large reddish purple-colored flowers with light purple-colored centers; and good postproduction longevity.

2 Drawing Sheets

Figure 1:
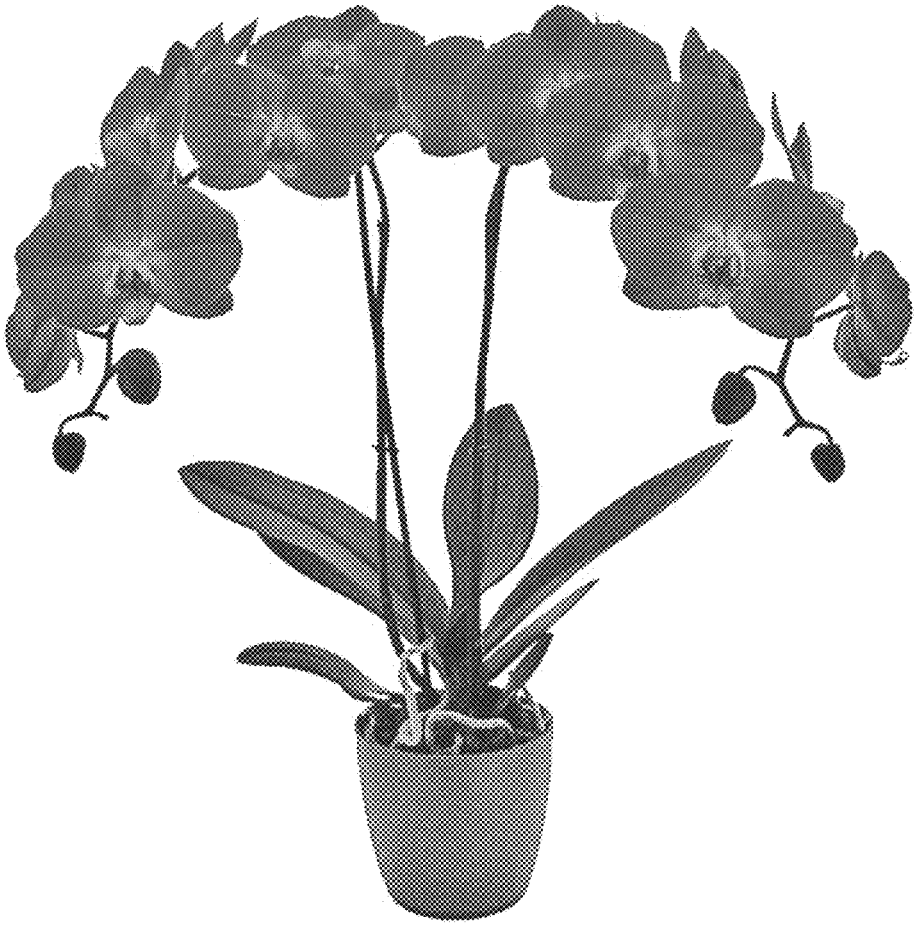

Botanical designation: x *Doritaenopsis* (*Doritis* x *Phalaenopsis*).

Cultivar denomination: 'LADY FANTASY'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Sep. 14, 2020, application number 2020/2152. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of x *Doritaenopsis* plant, botanically known as x *Doritaenopsis* (*Doritis* x *Phalaenopsis*), commonly referred to as *Doritaenopsis* and hereinafter referred to by the name 'Lady Fantasy'.

The new *Doritaenopsis* plant is a product of a planned breeding program conducted by the Inventor in Nantou, Taiwan and Heemskerk, The Netherlands. The objective of the breeding program is to develop new fast-growing and freely flowering *Doritaenopsis* plants with good leaf shape and large flowers with unique and attractive patterns and coloration.

The new *Doritaenopsis* plant originated from a cross-pollination in June, 2011 in Nantou, Taiwan of x *Doritaenopsis* 'Modern Valentine', not patented, as the female, or seed, parent with x *Doritaenopsis* 'Modern Rose', not patented, as the male, or pollen, parent. The new *Doritaenopsis* plant was discovered and selected by the Inventor as a single flowering plant from within the progeny of the stated cross-pollination grown in a controlled greenhouse environment in Heemskerk, The Netherlands in April, 2017.

Asexual reproduction of the new *Doritaenopsis* plant by in vitro meristem propagation in a controlled environment in Assendelft, The Netherlands since April, 2018 has shown that the unique features of this new *Doritaenopsis* plant are stable and reproduced true to type in successive generations.

SUMMARY OF THE INVENTION

Plants of the new *Doritaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Lady Fantasy'. These characteristics in combination distinguish 'Lady Fantasy' as a new and distinct *Doritaenopsis* plant:

1. Upright plant habit.
2. Moderately vigorous to vigorous growth habit.
3. Strong leaves.
4. Strong flowering stems.
5. Freely flowering habit with typically two inflorescences per plant, each inflorescence with numerous flowers.
6. Large reddish purple-colored flowers with light purple-colored centers.
7. Good postproduction longevity.

Plants of the new *Doritaenopsis* can be compared to plants of the female parent, 'Modern Valentine'. Plants of the new *Doritaenopsis* differ primarily from plants of 'Modern Valentine' in flower color as plants of the new *Doritaenopsis* have reddish purple-colored flowers with light purple-colored centers without distinct stripes or venation whereas plants of 'Modern Valentine' have white-colored flowers that are blushed with violet with dense and distinct stripes and venation.

Plants of the new *Doritaenopsis* can be compared to plants of the male parent, 'Modern Rose'. Plants of the new *Doritaenopsis* differ primarily from plants of 'Modern Rose' in flower form as flower petals of plants of the new *Doritaenopsis* are free to touching whereas flower petals of plants of 'Modern Rose' are completely free. In addition, cirrose tips of the labella (also referred to as "whiskers") of plants of the new *Doritaenopsis* are white and reddish purple in color whereas cirrose tips of the labella of plants of 'Modern Rose' are purple red in color.

Plants of the new *Doritaenopsis* can be compared to plants of x *Doritaenopsis* 'Ladies Day', disclosed in a Provisional U.S. Patent application Ser. No. 62/705,005 and in U.S. Plant patent application Ser. No. 17/340,014 filed concurrently. Plants of the new *Doritaenopsis* differ primarily from plants of 'Ladies Day' in growth habit as plants of the new *Doritaenopsis* are more vigorous than plants of 'Ladies Day'. In addition, plants of the new *Doritaenopsis* have larger flowers than plants of 'Ladies Day'.

Plants of the new *Doritaenopsis* can also be compared to plants of *Phalaenopsis hybrida* 'Purple Dust', disclosed in U.S. Plant Pat. No. 29,177. In side-by-side comparisons, plants of the new *Doritaenopsis* differ primarily from plants of 'Purple Dust' in flower color as plants of the new *Doritaenopsis* have reddish purple-colored flowers with light purple-colored centers whereas plants of 'Purple Dust' have purple/violet-colored flowers with a white-colored haze in the center. In addition, flowers of plants of the new *Doritaenopsis* are arranged on racemes whereas flowers of plants of 'Purple Dust' are arranged on panicles.

BRIEF DESCRIPTION OF THE PHOTOGRAPHS

The accompanying photographs illustrate the overall appearance of the new *Doritaenopsis* plant showing the colors as true as it is reasonably possible to obtain in colored reproductions of this type. Colors in the photographs may differ slightly from the color values cited in the detailed botanical description which accurately describe the colors of the new *Doritaenopsis* plant.

The photograph on the first sheet (FIG. 1) is a side perspective view of a typical flowering plant of 'Lady Fantasy' grown in a container.

Figure 2:
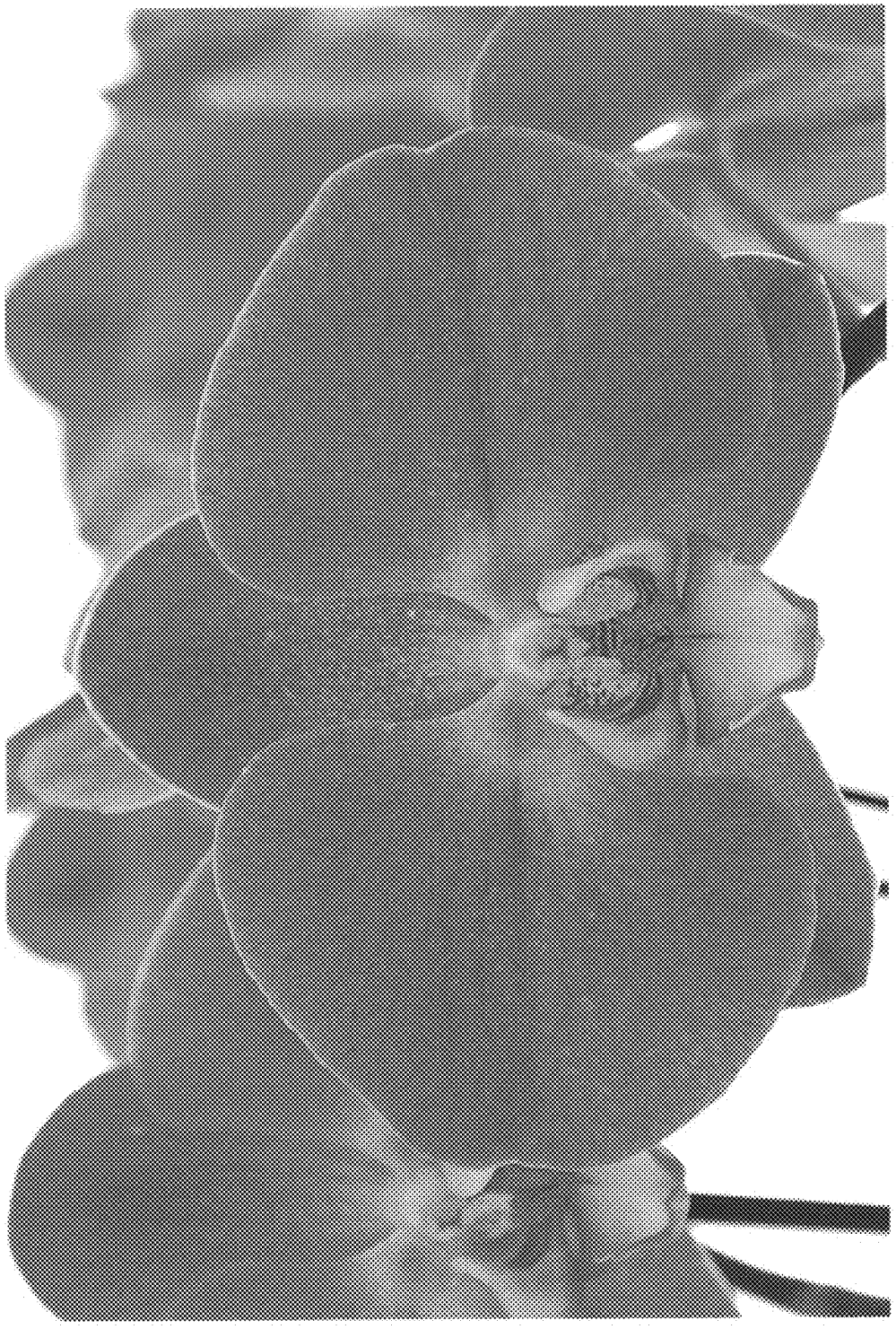

The photograph on the second sheet (FIG. 2) is a close-up view of a typical flower of 'Lady Fantasy'.

DETAILED BOTANICAL DESCRIPTION

The aforementioned photographs and following observations and measurements describe plants grown during the autumn in 10.5-cm containers in a glass-covered greenhouse in Heemskerk, The Netherlands and under cultural practices typically used in commercial *Doritaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: x *Doritaenopsis* (*Doritis* x *Phalaenopsis*) 'Lady Fantasy'.

Parentage:

*Female parent.*—x *Doritaenopsis* (*Doritis* x *Phalaenopsis*) 'Modern Valentine', not patented.

*Male parent.*—x *Doritaenopsis* (*Doritis* x *Phalaenopsis*) 'Modern Rose', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane.*—About 19.9 cm.

*Plant height, substrate level to top of inflorescences.*—About 46.4 cm.

*Plant diameter or spread.*—About 38.9 cm.

Leaf description:

*Arrangement and quantity.*—Distichous, simple; sessile; about seven leaves per plant.

*Length.*—About 22.4 cm.

*Width.*—About 7 cm.

*Aspect.*—Outwardly arching.

*Shape.*—Narrowly obovate to oblong and obovate; slightly carinate.

*Apex.*—Unequal broadly acute to unequal broadly obtuse.

*Base.*—Sheathing. Sheath length: About 1.8 cm. Sheath width: About 1.4 cm. Sheath color: Close to 146A strongly tinged with close to N186C.

*Margin.*—Entire.

*Texture and luster, upper and lower surfaces.*—Smooth, glabrous; slightly glossy.

*Venation pattern.*—Camptodromous.

*Color.*—Developing leaves, upper surface: Slightly darker than between NN137A and 147A; distal margin edges, tinged with close to N186A. Developing leaves, lower surface: Close to 146A to 147B; towards the margins and apex, strongly tinged with close to N186A. Fully expanded leaves, upper surface: Close to NN137B; apical margins, tinged with close to N199A;venation, close to NN137A. Fully expanded leaves, lower surface: Close to 146A; towards the margins and apex, strongly tinged with close to N186A; venation, close to between 146A and 147A.

Inflorescence description:

*Appearance and flowering habit.*—Showy zygomorphic flowers arranged on axillary branched racemes; typically two inflorescences per plant; each inflorescence with about twelve flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about four weeks on the plant; flowers not persistent.

*Inflorescence length* (*lowermost flower to inflorescence apex*).—About 33.2 cm.

*Inflorescence width.*—About 16.4 cm.

*Flower buds.*—Height: About 2 cm. Diameter: About 1.4 cm by 1.6 cm. Shape: Broadly ovate. Color: Close to between N79B and 187B.

*Flower size.*—Large, about 8.5 cm (vertical) by 10.4 cm (horizontal).

*Flower depth.*—About 3.2 cm.

*Petals, quantity and arrangement.*—Three, two lateral petals and one center petal transformed into a labellum.

*Lateral petals.*—Length: About 5 cm. Width: About 5.9 cm. Shape: Lunate to reniform. Apex: Shallowly retuse. Margin: Entire. Texture and luster, upper and lower surfaces: Smooth, glabrous, velvety; matte. Color: When opening, upper surface: Close to between N78B and NN78A and between N78B and NN78B; towards the base, close to 76D. When opening, lower surface: Close to N78B; towards the base, close to N78C. Fully opened, upper surface: Close to NN78A and between N78B and NN78B; towards the base, close to 76B; color does not change with subsequent development. Fully opened, lower surface: Close to N78B and N78C; towards the base, close to 76D; venation, close to NN78B; color does not change with subsequent development.

*Labella.*—Appearance: Three-parted with two lateral lobes and a central lobe. Length, lateral lobes: About 2.1 cm. Width, lateral lobes: About 1.6 cm. Length, central lobe: About 3.5 cm. Width, central lobe: About 7 mm to 24 mm. Size, cirrose tips: About 1 cm in length and about 1.7 mm in width. Shape, lateral lobes: Obovate. Shape, central lobe: Deltoid. Apex, lateral lobes: Obtuse. Apex, central lobe: Cleft with cirrose tips that are recurved. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 4 mm in length, about 6 mm in width and about 6 mm in height. Color: When opening, upper surface: Lateral lobes: Close to 76B; towards the apex, close to 76D; towards the base and basal margins, strongly tinged with close to 172B and 172C; at the base, stripes, close to 187C to 187D. Central lobe: Close to NN155D; towards the apex, close to N78C to N78D; towards the margins, close to 59B tinged with close to 162B and 162C; at the base (at column connection), close to 11D with stripes, close to 183A; cirrose tips, close to 77B. Callosities: Close to 16B and 16C densely covered with fine dots, close to 183A. When opening, lower surface: Lateral lobes: Close to 76C to 76D; towards the margins, close to N78C to N78D and basal margins, strongly tinged with close to 172B and 172C. Central lobe: Close to N78C; towards the margins, close to N78D and 59B; at the base (at column connection), close to 157A; cirrose tips, close to 77B. Fully opened, upper surface: Lateral lobes: Close to 76B; towards the margins, close to N75B and basal margin, strongly tinged with close to 172A to 172B; at the base, strongly tinged with close to 172A to 172B with stripes, close to 183B. Central lobe: Close to NN155D; towards the apex, close to N78D; towards the margins, close to 59A tinged with close to 162B; at the base (at column connection), close to 158A with stripes, close to 59A; cirrose tips, close to N78C. Callosities: Close to 13C densely covered with fine dots, close to 183B. Fully opened, lower surface: Lateral lobes: Close to N155D; towards the margins and apex, close to N75B to N75D and basal margins, strongly tinged with close to close to 172B. Central lobe: Close to N78C; towards the margins, close to 59A tinged with close to 162D; towards the base, close to NN78B and at the base (at column connection), close to 157B; cirrose tips, close to N78B.

*Sepals.*—Quantity and arrangement: Three, one upper dorsal sepal and two lower lateral sepals. Length, dorsal sepal: About 5 cm. Width, dorsal sepal: About 3.7 cm. Length, lateral sepals: About 4.8 cm. Width, lateral sepals: About 3.2 cm. Shape, dorsal sepal: Broadly elliptic to slightly obovate. Shape, lateral sepals: Ovate. Apex, dorsal sepal: Bluntly acute. Apex, lateral sepals: Bluntly acute to obtuse. Base, dorsal sepal: Truncate. Base, lateral sepals: Cuneate to truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to N78A; towards the base, close to 77D. When opening, lower surface: Close to N78B; central blotch, tinged with close to 72A. Fully opened, upper surface: Close to N78A; towards the base, close to 77D. Fully opened, lower surface: Close to N78B to N78C; central blotch, tinged with close to NN78A. Color, lateral sepals: When opening, upper surface: Close to N78A; towards the base, close to N78B to N78C, 77D and 154D; at the base, dense and fine dots, close to N79C. When opening, lower surface: Close to N78B to N78C; towards the base, tinged with close to 196A; main vein, close to N79C. Fully opened, upper surface: Close to N78A with fine dots, close to 76C; at the base, close to 157A heavily covered with fine dots, close to N79C. Fully opened, lower surface: Close to N78B; towards the base, close to N78C; at the base, tinged with close to 157A; main vein, slightly darker than NN78A.

*Peduncles.*—Length: About 62.5 cm. Diameter: About 6 mm. Strength: Strong. Aspect: Upright to outwardly arching. Texture and luster: Smooth, glabrous; matte. Color: Close to between 147A and 202A covered with fine dots, close to 147C.

*Pedicels.*—Length: About 4 cm. Diameter: About 3 mm. Strength: Moderately strong. Aspect: About 70° from peduncle axis. Texture and luster: Smooth, glabrous; matte. Color: Close to 197B to 197C; proximally, close to N199B and distally, close to 75B.

*Reproductive organs.*—Androecium: Column length: About 9 mm. Column width: About 6 mm. Column color: Close to NN155D; towards the apex, close to 75A. Pollinia quantity: Two. Pollinia diameter (per two pollinia): About 3 mm. Pollinia color: Close to 25B. Gynoecium: Stigma length: About 4 mm. Stigma width: About 5 mm. Stigma shape: Reniform. Stigma color: Close to N155A. Ovary length: About 7 mm. Ovary diameter: About 1 mm. Ovary color: Close to 157A. Seeds and fruits: To date, seed and fruit development have not been observed on plants of the new *Doritaenopsis*.

Pathogen & pest resistance: To date, plants of the new *Doritaenopsis* have not been shown to be resistant to pathogens and pests common to *Doritaenopsis* plants.

Temperature tolerance: Plants of the new *Doritaenopsis* have been observed to tolerate temperatures ranging from about 15° C. to about 40° C. and are suitable for USDA Hardiness Zones 10 to 12.

It is claimed:

1. A new and distinct *Doritaenopsis* plant named 'Lady Fantasy' as illustrated and described.

* * * * *